| (12) | United States Patent | (10) Patent No.: US 10,371,638 B2 |
|---|---|---|
| | Osman | (45) Date of Patent: Aug. 6, 2019 |

(54) FLUORESCENT MICROSCOPE

(71) Applicant: Indiana University Research and Technology Corporation, Indianapolis, IN (US)

(72) Inventor: Hany Osman, Indianapolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 15/739,152

(22) PCT Filed: Jul. 6, 2016

(86) PCT No.: PCT/US2016/041131
§ 371 (c)(1),
(2) Date: Dec. 21, 2017

(87) PCT Pub. No.: WO2017/007818
PCT Pub. Date: Jan. 12, 2017

(65) Prior Publication Data
US 2018/0372641 A1 Dec. 27, 2018

Related U.S. Application Data

(60) Provisional application No. 62/188,912, filed on Jul. 6, 2015.

(51) Int. Cl.
*G01N 21/64* (2006.01)
*A61B 90/20* (2016.01)
(Continued)

(52) U.S. Cl.
CPC ......... *G01N 21/6458* (2013.01); *A61B 90/20* (2016.02); *G02B 7/004* (2013.01); *G02B 21/16* (2013.01); *A61B 18/20* (2013.01); *A61B 18/203* (2013.01); *A61B 2017/00486* (2013.01); *A61B 2018/00577* (2013.01); *A61B 2018/00982* (2013.01); *G02B 21/26* (2013.01)

(58) Field of Classification Search
CPC ............ A61B 1/00188; A61B 1/00126; A61B 2090/3614; A61B 1/00154; A61B 90/36; A61B 90/50; G01B 9/0203; G01B 9/02091; G01N 21/645
USPC ...................................................... 250/459.1
See application file for complete search history.

(56) References Cited

U.S. PATENT DOCUMENTS

| 4,666,239 A | * | 5/1987 | Lidholt | ................ | G02B 6/3874 385/139 |
| 4,802,726 A | * | 2/1989 | Palmquist | ............. | B24B 19/226 385/134 |

(Continued)

OTHER PUBLICATIONS

Pierce, Mark, et al., "High-resolution Fiber-optic Microendoscopy for in situ Cellular Imaging", Journal of Visualized Experiments (JOVE); www.jove.com, e2306, Jan. 1, 2011, Issue 47; 5 pages.

(Continued)

*Primary Examiner* — Taeho Jo
(74) *Attorney, Agent, or Firm* — Faegre Baker Daniels LLP

(57) ABSTRACT

The present disclosure provides a method and system including a non-confocal microscope with an attached imaging fiber optic for direct and real time visualization of mammalian microscopic structures for diagnostic and therapeutic uses.

17 Claims, 17 Drawing Sheets

(51) Int. Cl.
  *G02B 21/16*  (2006.01)
  *G02B 7/00*  (2006.01)
  *A61B 18/20*  (2006.01)
  *G02B 21/26*  (2006.01)
  *A61B 18/00*  (2006.01)
  *A61B 17/00*  (2006.01)

(56) References Cited

U.S. PATENT DOCUMENTS

| | | | | |
|---|---|---|---|---|
| 5,459,564 | A * | 10/1995 | Chivers | G01B 9/04 356/477 |
| 9,841,579 | B2 * | 12/2017 | Baribault | H04N 5/2252 |
| 2001/0049258 | A1 * | 12/2001 | Erdogan | B24B 19/226 451/389 |
| 2004/0001253 | A1 * | 1/2004 | Abe | G02B 21/0088 359/388 |
| 2005/0024721 | A1 * | 2/2005 | Storz | G02B 21/002 359/385 |
| 2005/0168810 | A1 * | 8/2005 | Vodyanoy | G01J 3/44 359/368 |
| 2005/0237605 | A1 * | 10/2005 | Vodyanoy | G02B 21/10 359/385 |
| 2005/0258376 | A1 * | 11/2005 | Takatsuka | G01N 21/6428 250/458.1 |
| 2006/0257993 | A1 | 11/2006 | McDevitt et al. | |
| 2007/0291798 | A1 * | 12/2007 | Kenny | G02B 21/06 372/6 |
| 2008/0019656 | A1 * | 1/2008 | Zhou | G02B 6/3833 385/136 |
| 2010/0290744 | A1 * | 11/2010 | Zhou | G02B 6/3833 385/89 |
| 2012/0062987 | A1 | 3/2012 | Hnatkoyich et al. | |
| 2013/0038864 | A1 | 2/2013 | Flora et al. | |
| 2014/0036258 | A1 * | 2/2014 | Nakamura | G01M 11/31 356/153 |
| 2014/0063598 | A1 * | 3/2014 | Zhou | G02B 6/3866 359/368 |
| 2014/0082775 | A1 * | 3/2014 | Zahl | B82Y 35/00 850/6 |
| 2014/0187967 | A1 | 7/2014 | Wood et al. | |
| 2014/0192405 | A1 * | 7/2014 | Jaffe | G02B 27/30 359/379 |
| 2014/0268109 | A1 * | 9/2014 | Eckman | G01B 9/0203 356/73 |
| 2014/0268318 | A1 * | 9/2014 | Mandella | G02B 21/0048 359/364 |
| 2015/0338583 | A1 * | 11/2015 | Valencia | G02B 6/3873 385/59 |
| 2016/0341904 | A1 * | 11/2016 | Morin-Drouin | G02B 6/385 |
| 2017/0035275 | A1 * | 2/2017 | Yajima | G02B 6/36 |
| 2018/0284358 | A1 * | 10/2018 | Lu | G02B 6/3849 |

OTHER PUBLICATIONS

International Search Report and Written Opinion issued by the ISA/US, Commissioner for Patents, dated Nov. 15, 2016, for International Application No. PCT/US2016/040527; 6 pages.

International Search Report and Written Opinion issued by the ISA/US, Commissioner for Patents, dated Sep. 23, 2016, for International Application No. PCT/US2016/ 041131; 7 pages.

* cited by examiner

FLUORESCENT MICROSCOPE

CROSS-REFERENCE TO RELATED APPLICATIONS

This application is a U.S. National Stage Application of International Patent Application No. PCT/2016/041131, filed Jul. 6, 2016, which claims the benefit of U.S. Provisional Patent Application Ser. No. 62/188,912, filed Jul. 6, 2015, each of which is expressly incorporated by reference in its entirety.

FIELD OF THE DISCLOSURE

This present disclosure generally relates to fluorescent microscopes and more specifically to a non-confocal microscope with an attached imaging fiber optic for direct and real time in-situ visualization of microscopic structures for diagnostic uses as well as direct and simultaneous tissue treatment for therapeutic uses, and methods of using the same. The methods may be undertaken in-vivo or ex-vivo. The methods may be non-invasive.

BACKGROUND OF THE DISCLOSURE

Obtaining biopsy samples or removal of pathologies and tumors from patients normally relies primarily on the gross evaluation, (either visual, palpation, or other gross methods) of the area to be biopsied or removed. Microscopic confirmation or validation of the biopsy or removed tissue occurs after the pathologist obtains the specimen. The processing of pathology samples is conventionally done through a multi-step process that includes grossing, tissue fixation, processing, embedding, cutting and staining before the tissue is viewable under the microscope. This process often requires several hours. Also, a similar process known as "frozen sections" involves the same steps, however may be performed in several minutes.

Current sampling and excisional methods of both live or ex-vivo tissues lack the ability to screen, visualize or confirm the sample microscopically during or before submitting a sample. Methods include, but are not limited to, obtaining biopsies, ablative treatments, removing tumors with no residual tumor at margins, and sampling tissue by gross pathological evaluation. Furthermore, there currently does not exist a method for simultaneous fiber optic in-vivo or ex-vivo pathologic examination for diagnosis and treatment using an ablative energy source such as laser. The ability of simultaneously diagnosing and treating tissue in the same session without the need to displace or replace the apparatus may enhance treatment precision and completeness. Failure of accurate diagnosis or treatment may result in inaccuracies during sampling and inaccurate pathological evaluation of specimens that may result in patient harm. Accordingly, a simple method for visualizing and treating specimens in-vivo or ex-vivo without any significant alteration of the specimen and in real-time for guiding biopsy, tissue removal or sampling is needed. Such a method (and corresponding apparatus) may reduce sampling or excisional errors or eliminate the need for a biopsy or physical sampling of a specimen.

SUMMARY OF THE DISCLOSURE

In one aspect, the present disclosure provides adapters for microscopes, including wide-field fluorescent microscopes, confocal microscopes or other microscope systems utilizing an objective lens for magnification. The adapters may include a fiber-optic connecter, a lateral adjustment connector in mechanical communication with the fiber-optic connecter, wherein the lateral adjustment connecter is configured to adjust the fiber-optic connecter laterally, and a vertical adapter configured to move the fiber-optic connecter along an image acquisition axis.

In various aspects, the adapter may be configured to transport an ablative energy along the image acquisition axis. The ablative energy may include ablative energy from a laser, light emitting diode, optically transmitted radiation or a combination thereof. The ablative energy may be a laser. In some aspects, the adapter is configured to mechanically communicate with an objective holder. In some aspects, the image acquisition axis and an optical axis of an objective in mechanical communication with the objective holder are aligned when the adapter is coupled to the objective holder. The objective holder may be configured to mechanically communicate with a 20× objective.

In another aspect, systems including a plurality of fluorescent microscopes, wherein a first fluorescent microscope comprises a first fiber-optic adapter connected to a first fiber-optic; and a second fluorescent microscope comprises a second fiber-optic adapter connected to a second fiber-optic, wherein the first fiber-optic and the second fiber-optic are in mechanical communication, are disclosed. The adapters may include a fiber-optic connecter, a lateral adjustment connector in mechanical communication with the fiber-optic connecter, wherein the lateral adjustment connecter is configured to adjust the fiber-optic connecter laterally, and a vertical adapter configured to move the fiber-optic connecter along an image acquisition axis. The field of view of the first fiber-optic and a field of view of the second fiber-optic may form a larger field of view in various aspects. The system may comprise a channel for ablative energy. The fiber-optic may be configured to channel the ablative energy. The ablative energy may be a laser. In some aspects, the system may be configured to generate a three-dimensional image. In some aspects, the system comprises a plurality of fiber-optics configured to alter a viewing angle, a field of view, or both.

The system may be configured to provide a larger field of view where at least a portion of two or more objective fields of two of the plurality of microscopes are combined according to various aspects.

The system may be configured so that ablative energy is directed through the individual microscopes and fiber optic probes to cover the areas of interest and spare areas not intended for ablation within the same field.

In some aspects, at least one fluorescent microscope of the plurality of fluorescent microscopes may comprise a tube lens and an image acquisition device. The microscope may have a ratio X that is between 0.5 and 1.5, where $$X = \frac{\text{Distance from a proximal end of the fiber-optic and the tube lens}}{\text{Distance from the tube lens and the image acquisition device}}.$$

Various methods are also provided for evaluating a specimen. The methods may include routing a first light having a wavelength that causes a fluorescent dye applied to a specimen to fluoresce through a microscope having an imaging fiber optic coupled to a magnifying objective and having a distal tip disposed adjacent the specimen, routing a second light emitted from the specimen through the microscope to the magnifying objective, and generating an image of the specimen using an image acquisition device, wherein the microscope comprises an adapter. The adapter may comprise a fiber-optic connector, a lateral adjustment connector in mechanical communication with the fiber-optic connector, wherein the lateral adjustment connector is configured to adjust the fiber-optic connector laterally, and a vertical adapter configured to move the fiber-optic connector along an image acquisition axis. The method may also comprise treating the specimen via ablative energy. In some aspects, the adapter may be any adapter as described herein.

In any of the aspects of the present disclosure, the specimen may be a mammalian tissue. The tissue may be a tumor. The tissue may have been excised from the mammal before evaluation (ex-vivo) or may be evaluated in-situ (in-vivo).

There is also provided a microscope comprising the adapter according to any of the aspects disclosed herein. The microscope may comprise a tube lens and an image acquisition device, and have a ratio X that is between 0.5 and 1.5, where $$X = \frac{\text{Distance from a proximal end of the fiber-optic and the tube lens}}{\text{Distance from the tube lens and the image acquisition device}}.$$

It will be appreciated that numerous modifications to the abovementioned aspects and aspects of the present disclosure may be made without departing from the scope of the disclosure as defined in the appended claims. Moreover, any one or more of the above described preferred aspects could be combined with one or more of the other preferred aspects to suit a particular application.

Optional and/or preferred features may be used in other combinations beyond those described herein, and optional and/or preferred features described in relation to one aspect or aspect of the present disclosure may also be present in another aspect or aspect of the present disclosure, where appropriate.

The described and illustrated aspects are to be considered as illustrative and not restrictive in character, it being understood that only the preferred aspects have been shown and described and that all changes and modifications that come within the scope of the disclosure(s) as defined in the claims are desired to be protected. It should be understood that while the use of words such as "preferable", "preferably", "preferred" or "more preferred" in the description may suggest that a feature so described may be desirable, it may nevertheless not be necessary and aspects lacking such a feature may be contemplated as within the scope of the present disclosure as defined in the appended claims. In relation to the claims, it is intended that when words such as "a," "an," or "at least one," are used to preface a feature there is no intention to limit the claim to only one such feature unless specifically stated to the contrary in the claim.

BRIEF DESCRIPTION OF THE DRAWINGS

The above-mentioned and other features of this disclosure and the manner of obtaining them will become more apparent and the disclosure itself will be better understood by reference to the following description of aspects of the present disclosure taken in conjunction with the accompanying drawings, wherein.

DETAILED DESCRIPTION

Figure 1A:
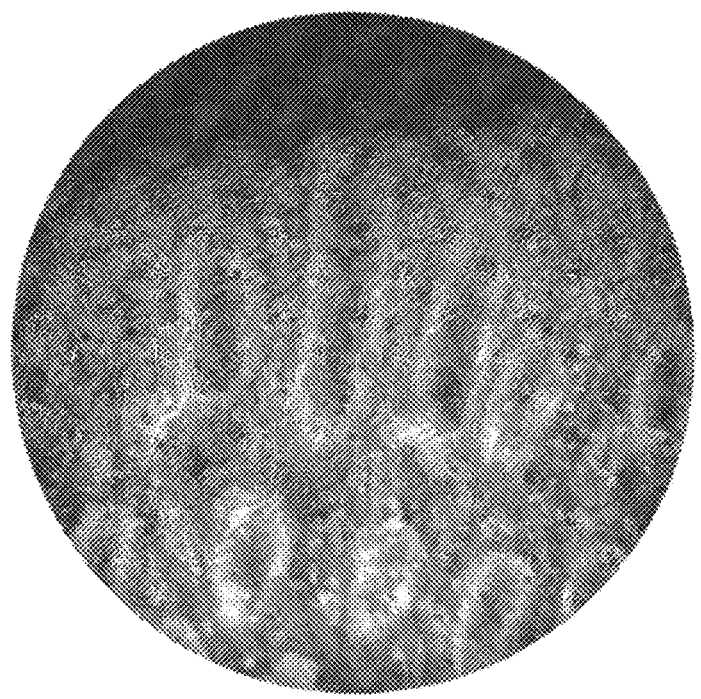
FIGS. 1A and 1B show views of a specimen using a microscope according to the present disclosure.

The aspects disclosed herein are not intended to be exhaustive or to limit the disclosure to the precise forms disclosed in the following detailed description. Rather, the aspects were chosen and described so that others skilled in the art may utilize their teachings.

As used herein, the modifier "about" or "approximately" used in connection with a quantity is inclusive of the stated value and has the meaning dictated by the context (for example, it includes at least the degree of error associated with the measurement of the particular quantity). When used in the context of a range, the modifier "about" should also be considered as disclosing the range defined by the absolute values of the two endpoints. For example, the range "from about 2 to about 4" also discloses the range "from 2 to 4."

As further described below, the present disclosure provides a microscope which works in a similar way to a simple fluorescent microscope with an attached imaging fiber optic. The microscope may also provide multiple channels for additional imaging of wavelengths or simultaneous ablation or treatment of tissues. The imaging fiber optic is composed of multiple smaller optic fibers that serve to transmit image data at a microscopic level. The microscope includes a light source(s) (exemplified as excitation energy 220 in FIGS. 2A and 2B) that emit light at a specific wavelength. The light is passed through a filter and condensing lens and is then channeled via a dichroic mirror into the objective. The light then passes through the fiber optic and onto the specimen. The specimen may be prepared by adding fluorescent dyes such as acridine orange to allow for better visualization. The tissue emits an excitation signal at a different wavelength that is transported via the imaging fiber optic to the objective lens, dichroic mirror, emission filter and lens to be focused on the sensor of a camera. The fiber optic attachment to the objective lens offers 3 axis focus and positioning to allow focusing to the base of the fiber optic probe. The light source is housed in a structure that allows for the attachment of a heat sink, the condensing lens and the excitation filter.

As such, the present disclosure provides a method and apparatus for image acquisition of biological tissue using a fiber optic integrated with a simple fluorescent microscope. The current system integrates a simple fluorescent set up for image acquisition, however the adapter shown in FIG. 14A, B and FIG. 15 may be used to attach an imaging fiber optic probe microscope systems including confocal microscopes for diagnostic and therapeutic purposes. Also, the current system may integrate additional channels that may include ablative sources for simultaneous imaging and treatment of tissues. The images obtained via the present fluorescent microscopy are in their native three-dimensional architecture. As indicated above, the images are generated by exciting the tissue using continuous light emitted from a light source. The light is channeled to a magnifying objective lens and is then carried via an imaging optic fiber to the tissue. The light excites the tissue which in turns emits light at a different wavelength to be carried back through the imaging optic fiber and the objective to be channeled and focused on the image sensor of an image acquisition device such as a camera. The system may be used directly by placing the free end of the fiber optic into contact with the tissue and imaging the tissue without addition of fluorescent agents and using the inherent physical properties in the tissue and auto-fluorescence. A fluorescent dye may be applied to the tissue to enhance visualization. The dye may either be specific to a certain disease or attach to the cellular structures in a non-specific manner. The wavelength of the light emitted by the light source(s) is selected according to the excitation bandwidth of the dye used. Different dyes may be used with easily interchangeable filters and LEDs in the microscope. The objective magnification power may be changed with an accommodating focusable fiber optic adaptor.

The microscope may be composed of the following main components as is described in greater detail with reference to the figures of the present application.

Light source housing: The light source housing holds a light emitting diode (LED) with an attached heat sink to dissipate heat. The wavelength of the light emitted is selected according to the characteristics of the dyes used on the tissue. The divergent light emitted from the LED is focused using a condenser lens, and filtered to a narrow bandwidth using an excitation filter. A slot allows for an easily interchangeable filter or lens if needed. The light then enters the filter housing.

Filter housing: In one aspect, the filter housing consists of a configuration that brings the excitation light produced from the light source at a right angle to the image acquisition axis. The excitation light may be reflected via a dichroic mirror placed at approximately a 45 degree angle. The dichroic mirror may be placed with the aid of an adjustable dichroic mirror holder (shown as 82 in FIG. 10). The dichroic mirror may be selected to be reflective to the wavelength of the excitation light produced by the LED and transparent/translucent to the light emitted by the tissue.

Objective and fiber optic: The magnifying objective lens may be placed in line with the image acquisition axis. The light produced from the LED is reflected off the dichroic mirror and enters the base of the objective. The objective lens magnification power may vary. For example a 5×-40× objective lens may be used in certain aspects. A fiber optic may be then attached to the fiber optic holder (shown as 210 in FIGS. 2A and 2B) via a connector. The fiber optic used is an imaging fiber optic that includes a bundle composed of multiple smaller fibers. The number of fibers within the fiber optic may affect the resolution of the resultant image. The distance between the base of the fiber optic bundle (the proximal end) and the tube lens may be adjustable via a screw mechanism to allow the focusing of the excitation light into the base of the fiber optic and the emitted light from the base of the same fiber optic from/to the objective lens. The base of the fiber optic bundle may also be translated perpendicular to the image acquisition axis to allow for fine adjustment of the fiber optic location within the objective's field of view. The free end of the fiber optic may be the placed in contact with the tissue to be imaged.

Camera tube: The camera tube contains an adaptor that permits the attachment of a complementary metal-oxide-semiconductor (CMOS)—such as a consumer DSLR camera—or a charge-coupled device (CCD) camera—such as scientific grade cameras—to the system. The tube may have a slot that accommodates the placement of a magnifying tube lens 216 and an emission filter 218 (shown in FIGS. 2A and 2B). The slots may permit easy interchangeability of a filter or lens, if needed, for example via a lens and filter tray. This may allow for the use of different fluorescent dyes with different excitation/emission wavelengths. The length of the tube is determined by the power of the magnifying lens to bring the image into focus in the camera.

As is also further described below, the microscope has several applications for in-vivo and ex-vivo tissue evaluation. Examples are provided below.

Ex-vivo specimens: The first example is microscopic evaluation of disease at "grossing." Pathologists often rely on gross eye examination to determine dimensions, extension, and involvement of different anatomic structures, etc. of diseases such as tumors. This process is known as grossing. Accuracy of information obtained using gross examination is essential for staging and potentially correct treatment of patients. The microscope of the present disclosure permits the pathologist to directly and accurately obtain information about the tumor dimensions and extension at a microscopic level, that is otherwise not possible using prior art techniques. The present disclosure may even be used to obtain diagnoses and replace conventional methods of histology which often require several hours of tissue processing, embedding in paraffin wax, slicing and staining.

In a second example of ex-vivo tissue evaluation, the present disclosure provides improved sampling. The accuracy of evaluation of tissues by pathologists is often hindered by the gross sampling capabilities of the pathologist. Gross evaluation of a specimen to determine areas of the specimen to be sampled is an insensitive method of tissue sampling, however it is also the current method used in practice due to lack of the ability to directly evaluate tissues at the microscopic level. The present disclosure therefore offers a valuable tool to pathologists to evaluate tissue and uncover pathology that is otherwise missed with the naked eye.

In-vivo specimens: In-vivo microscopy or microscopic evaluation of tumor margins in an intra-operative setting using the present disclosure allows the pathologist and surgeon the flexibility of microscopically evaluating specimens in their native three dimensional state "as is," and at an improved turnaround time. Evaluating the tissue in-vivo inside the patient is possible and allows for a dramatically enhanced localization of areas that may be involved with a tumor left behind after tumor removal (or positive margins). The present disclosure may be used to evaluate pathology in various clinical settings (such as cervical screening and oral examinations), and may also be incorporated in endoscopes to enhance endoscopic evaluation of tissues.

The addition of ablative energy sources in the additional channel within the microscope allows for the possibility of simultaneously imaging and treating the tissues. This allows for microscopic precision of the ablative energy in treating tissues such as tumors.

The present application provides applications of 3D design and printing as an inexpensive method for providing the framework of a fiber optic fluorescent microscope. 3D printing permits the development of highly customizable and unique structural and mechanical parts at extremely low costs. It also allows for the reproduction and modification of the microscope according to the present disclosure for various experiments and applications using off-the-shelf components.

Figure 1B:
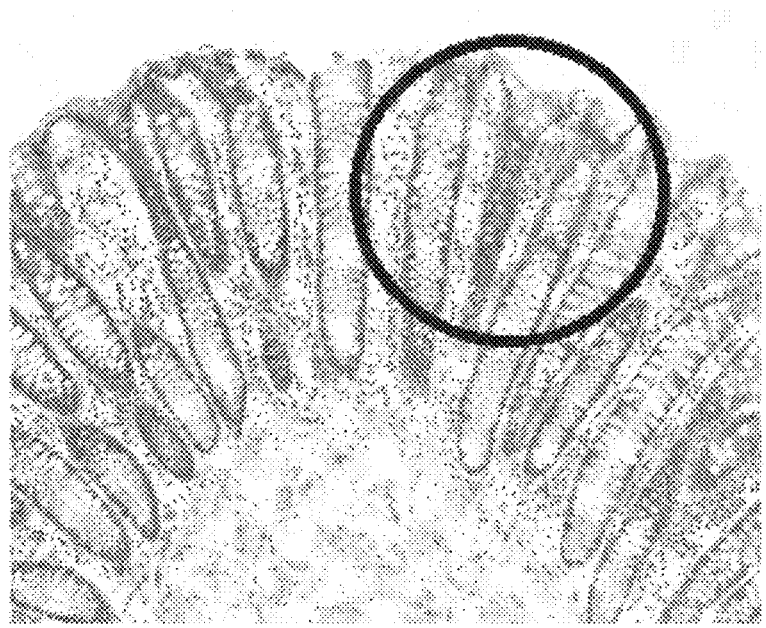

In one aspect of the present disclosure, an XYZ, da Vinci 1.0 3D printer is used for printing and Blender 3D modelling software was used for designing the parts. A Cannon T2i digital single lens reflection (DSLR) camera was used for the image acquisition, and a 20× objective, dichroic mirror, excitation and emission filters and tube lens are used as shown in the described figures. The filters and light emitting diode (LED) were selected for utility with acridine orange fluorescent dye, which was applied to the tissue to be viewed. An imaging fiber optic probe was attached to the objective using 3D printed parts for in-vivo or in-situ visualization. The other end was placed on the specimen, such as the specimen 5 exemplified in FIGS. 2A and 2B. Examples of the resulting images captured by the system are shown in FIGS. 1A and 1B. FIG. 1A, colonic crypts are shown using the present microscope after application of acridine orange, and FIG. 1B shows the corresponding hematoxylin and eosin processed slide.

The 3D printed components include a filter housing, which holds the dichroic mirror, objective and fiber optic holder that attaches to, or may be continuous with the filter housing, a camera tube and the light source housing. The 3D printed light source collimator may accommodate the excitation energy 220 and heat sink and also holds an excitation filter and a condenser lens. A condenser lens may be placed at a distance according to its focal length for partial collimation of the light from the light source to the base of the objective lens. The camera tube was designed with a base adaptor that inserts into the DSLR camera and has slots that hold the emission filter and tube lens. The camera tube and filter housing were printed in black plastic to minimize external light noise.

Figure 2A:
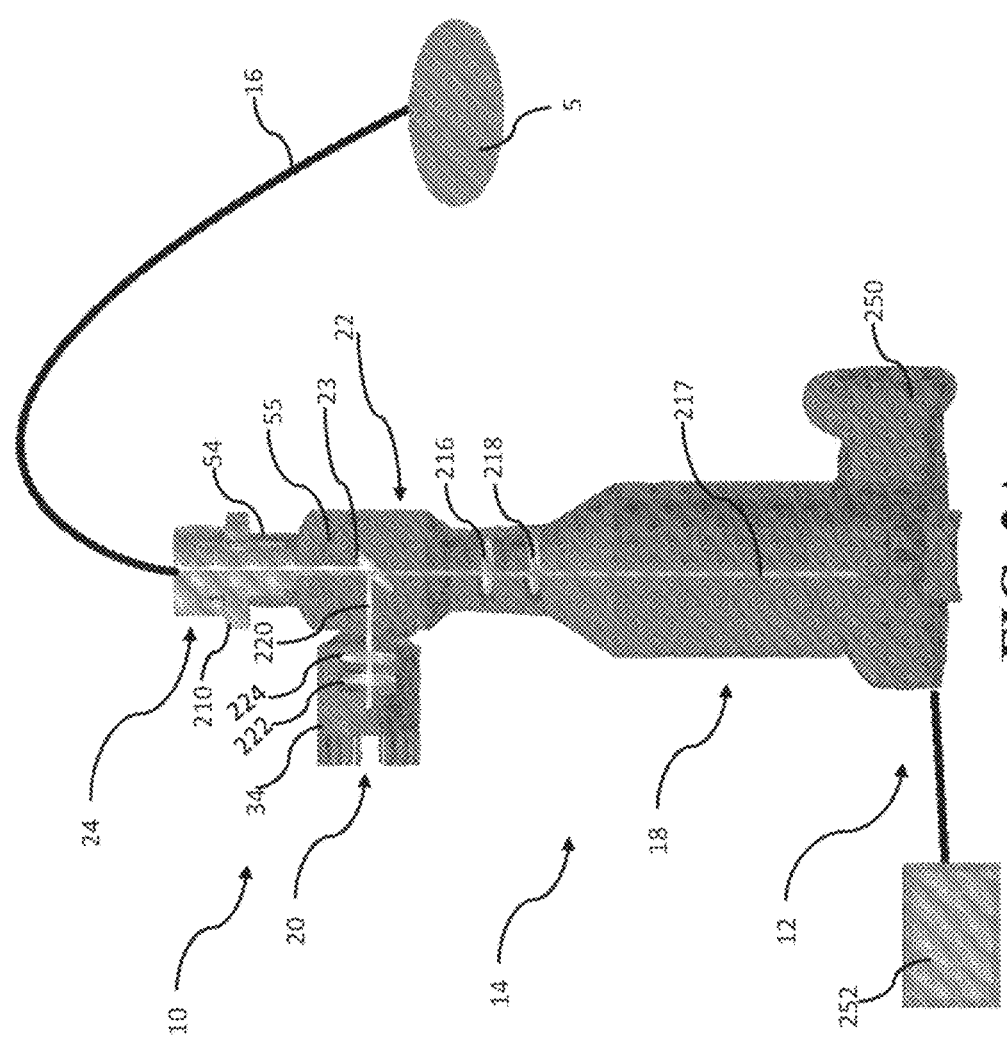
FIG. 2A is a schematic diagram of a microscope system according to one aspect of the present disclosure.
Figure 2B:
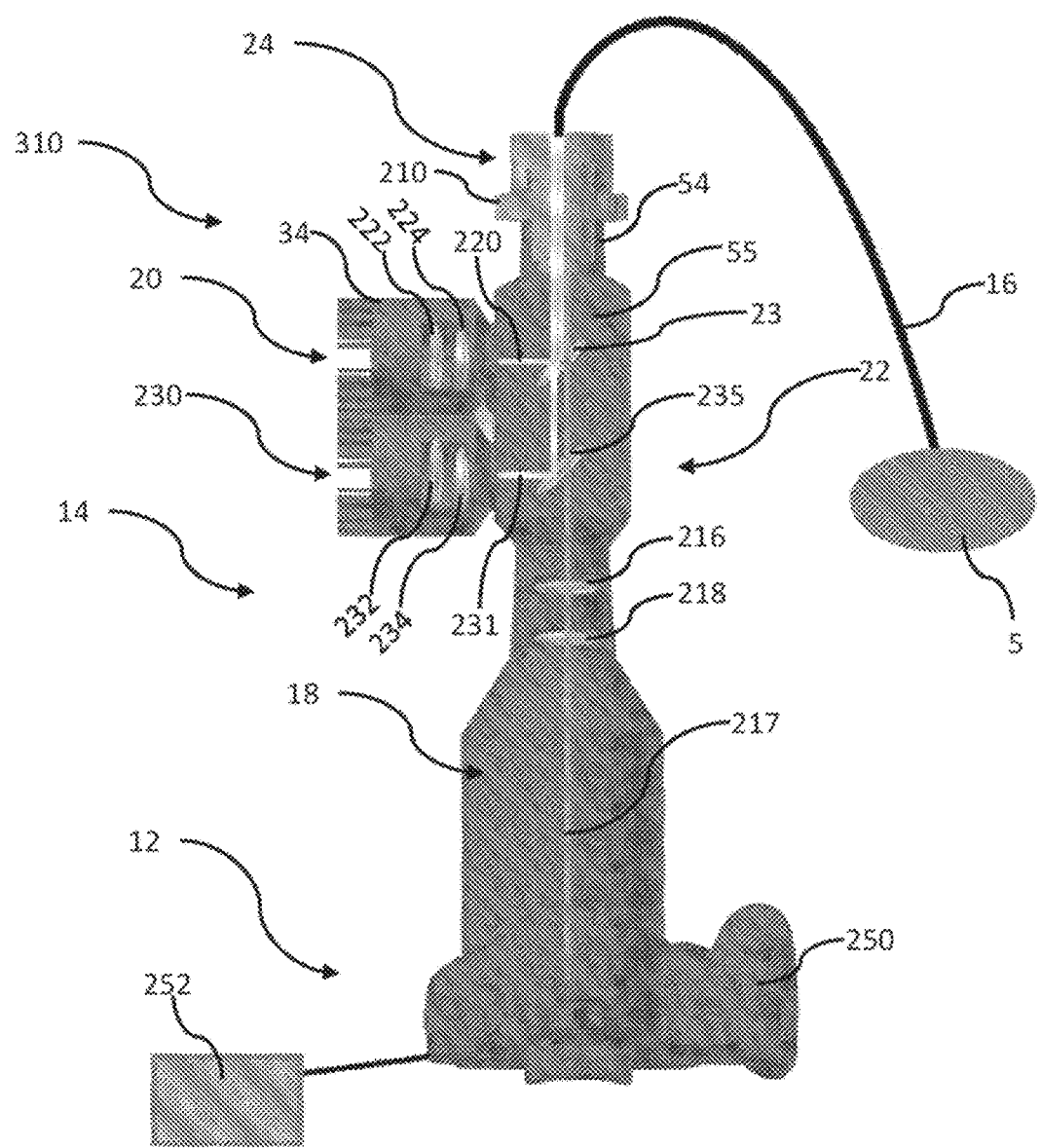
FIG. 2B is a schematic diagram of a microscope system comprising an ablative energy assembly according to one aspect of the present disclosure.

Referring now to FIGS. 2A and 2B, microscope systems 10 and 310 respectively according to certain aspects of the present disclosure are shown. Systems 10 and 310 may generally include an image acquisition device 12, such as the camera 250 described above, a microscope 14, and an imaging fiber optic 16. Microscope 14 generally includes a camera tube 18, a light source assembly 20, a filter housing 22, and an objective assembly 24. As shown, camera tube 18, light source assembly 20, and objective assembly 24 are each connected to filter housing 22. The emission light 217 from specimen 5 may travel from imaging fiber optic 16 and to the image acquisition device 12.

System 310, shown in FIG. 2B, may also include an ablative energy source assembly 230, which may comprise an ablative condenser 232 and an ablative filter 234. Ablative energy 231 may pass through the ablative condenser 232 and the ablative filer 234 and be reflected by ablative dichroic mirror 235. In various aspects of this disclosure, the inclusion of the ablative energy source assembly and the ablative dichroic mirror may allow for simultaneous diagnosis and treatment.

Figure 3:
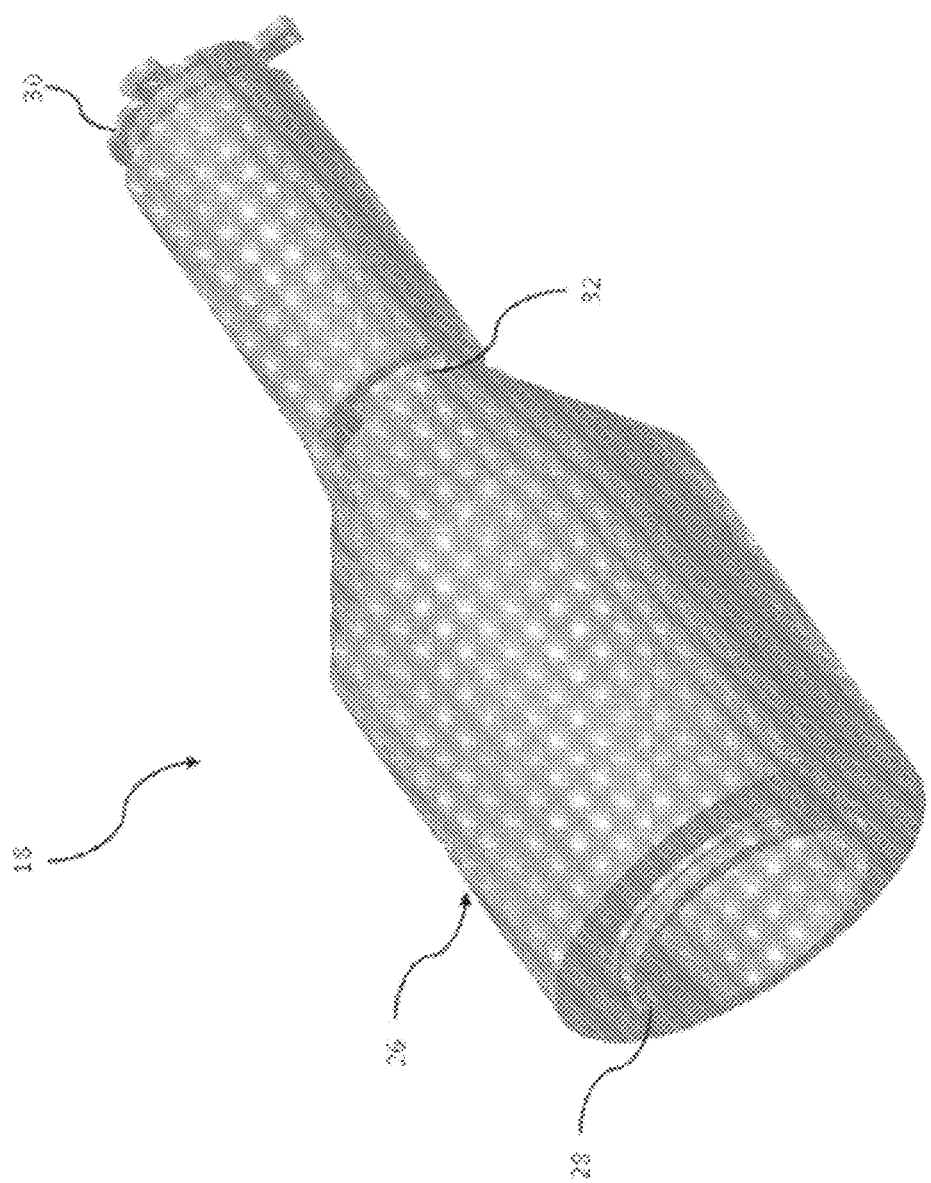
FIG. 3 is a perspective view of a camera tube of the microscope system of FIGS. 2A and 2B.

As best shown in FIG. 3, camera tube 18, which may be 3D printed as indicated above, includes a body 26 having one end 28 adapted to attach to image acquisition device 12 and another end 30 adapted to couple to filter housing 22. Body 26 further includes a slot 32 configured to receive a magnifying tube lens and an emission filter as depicted in FIGS. 2A and 2B. As indicated above, the overall length of camera tube 18 is determined by the power of the magnifying lens used to bring the image into focus. Integration of the ablative channel within each microscope within the assembly shown in FIG. 13 may allow for area selective ablation.

Figure 4:
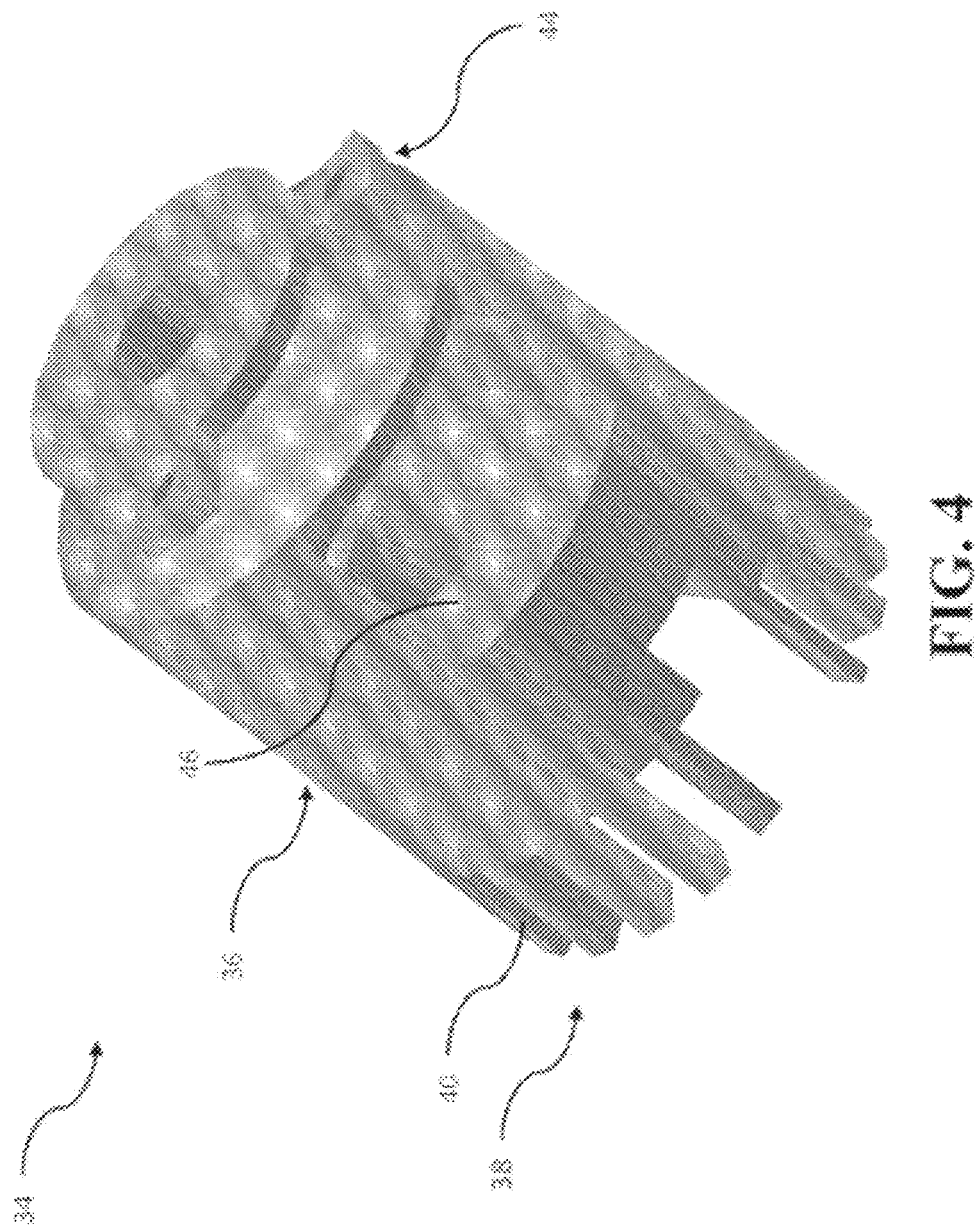
FIGS. 4 and 5 are perspective views of a light source housing of the microscope system of FIGS. 2A and 2B.
Figure 5:
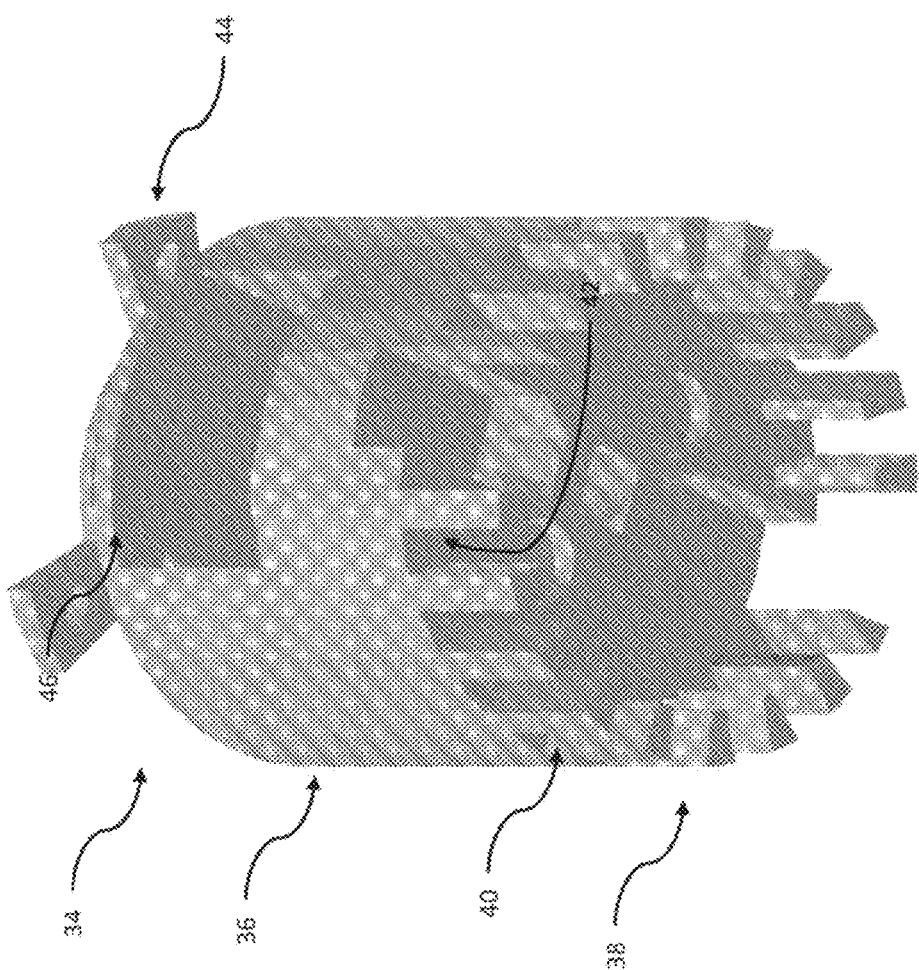

Referring now to FIGS. 4 and 5, a light source housing 34 of light source assembly 20 is shown. Light source housing 34, which may be 3D printed as indicated above, includes a body 36 having one end 38 with heat dissipation fins 40, an interior chamber 42 configured to receive a light source to produce excitation energy 220, which may pass through a condensing lens 222 and excitation filter 224, as depicted in FIGS. 2A and 2B, and another end 44 configured to couple with filter housing 22. As indicated above, the divergent light emitted from the LED may be focused using the condenser lens and filtered to the desired bandwidth using the excitation filter. Body 36 further includes a slot 46 to facilitate interchangeability of the lens and the filter.

Figure 6:
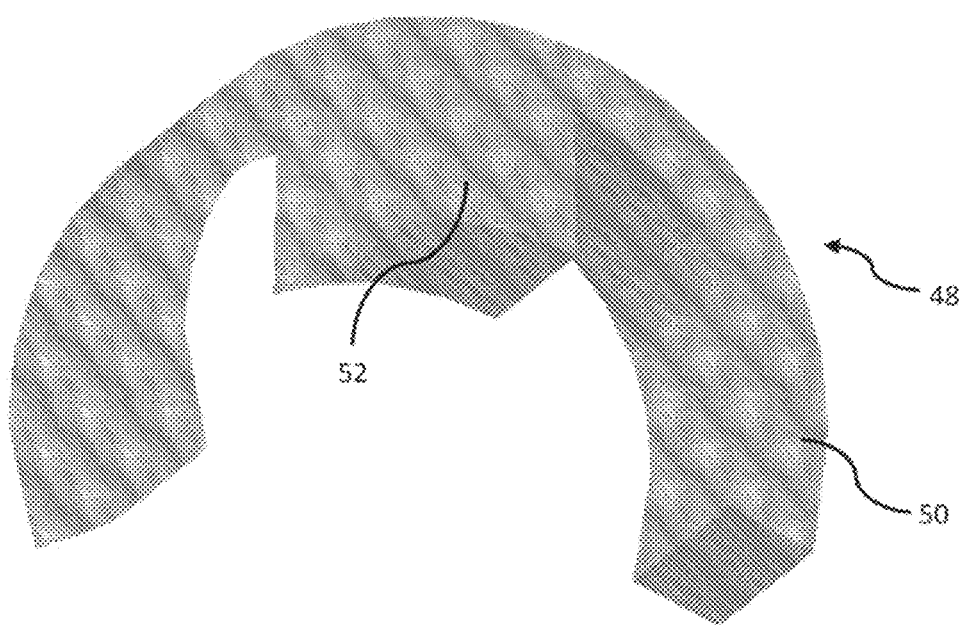
FIG. 6 is a perspective view of a light source slot cover of the microscope system of FIGS. 2A and 2B.

When system 10 is in operation, slot 46 may be covered by light source slot cover 48 depicted in FIG. 6. Light source slot cover 48, which may be 3D printed as indicated above, includes a curved body 50 which is sized to snap onto light source housing 34 and a projection 52 which is sized to fit into and cover slot 46 of the body 36 of light source housing 34.

Figure 7:
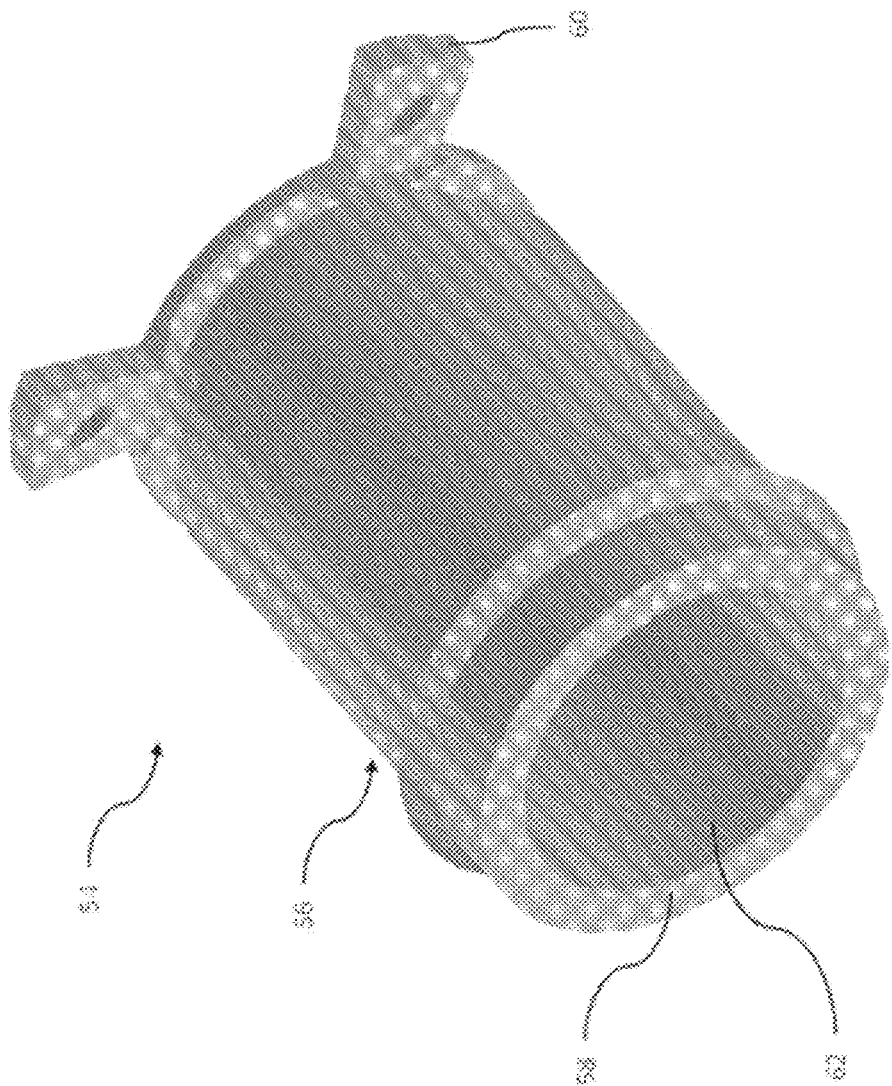
FIG. 7 is a perspective view of an objective holder of the microscope system of FIGS. 2A and 2B.

Referring now to FIG. 7, an objective holder 54 of objective assembly 24 is shown. Objective holder 54, which may be 3D printed as indicated above, includes a substantially cylindrical body 56 having one end 58 configured to couple to a fiber optic adapter as described below, another end 60 configured to couple with filter housing 22 and an interior chamber 62 for receiving the objective lens 55 as described above. The chamber 62 may be fitted to snap onto the objective lens or secured with tightening screws.

Figure 8:
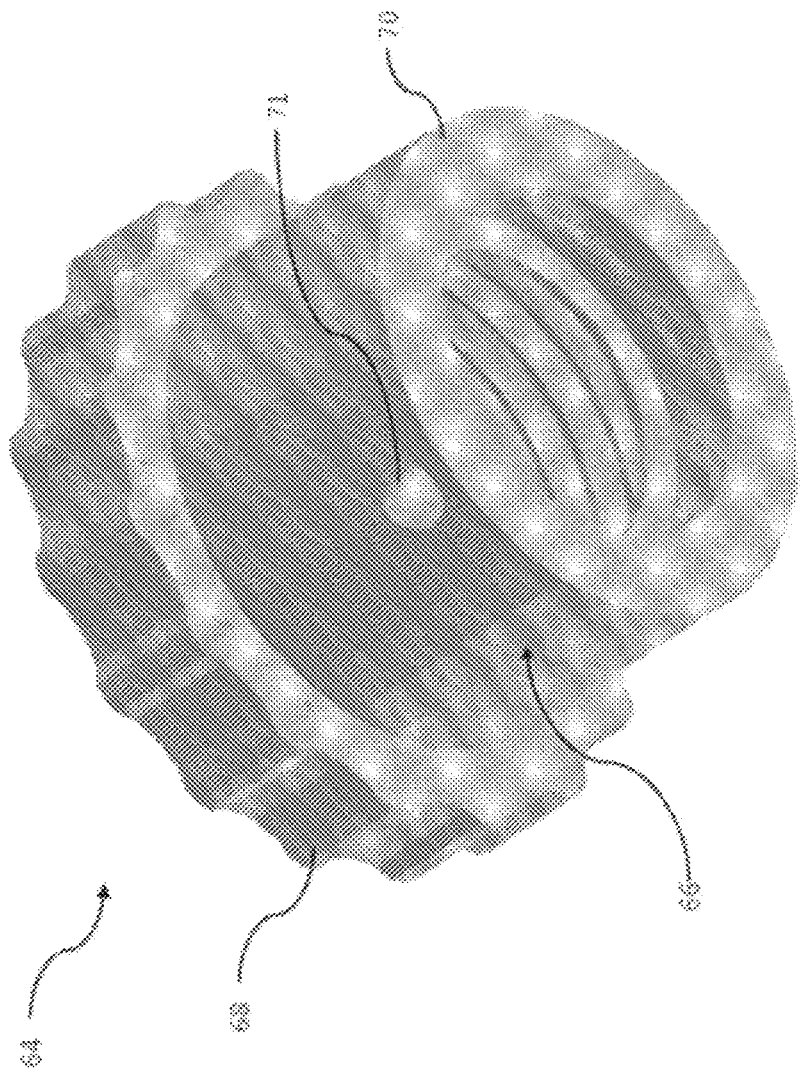
FIG. 8 is a perspective view of a fiber optic adapter of the microscope system of FIGS. 2A and 2B.

FIG. 8 depicts one aspect of a fiber optic adapter 64 of objective assembly 24. Fiber optic adaptor 64, which may be 3D printed as indicated above, includes a body 66 having one end 68 adapted to mate with end 58 of objective holder 54 and another end 70 adapted to receive imaging fiber optic 16. The fiber optic may be coupled with a female subminiature connector A ("SMA") threading that fits into a male counterpart housed within fiber optic adaptor 64. As indicated above, the base of imaging fiber optic 16 may be adjusted toward and away from the objective lens by rotating fiber optic adapter 64 to permit focusing of excitation light into imaging fiber optic 16 and the light emitted from the base of imaging fiber optic 16 to the objective lens. Furthermore, fiber optic adapter 64 may comprise adjustment bores 71, which may be configured to adjust the imaging fiber optic 16 in a plane perpendicular to the image acquisition axis (e.g., with screw 73).

Figure 9:
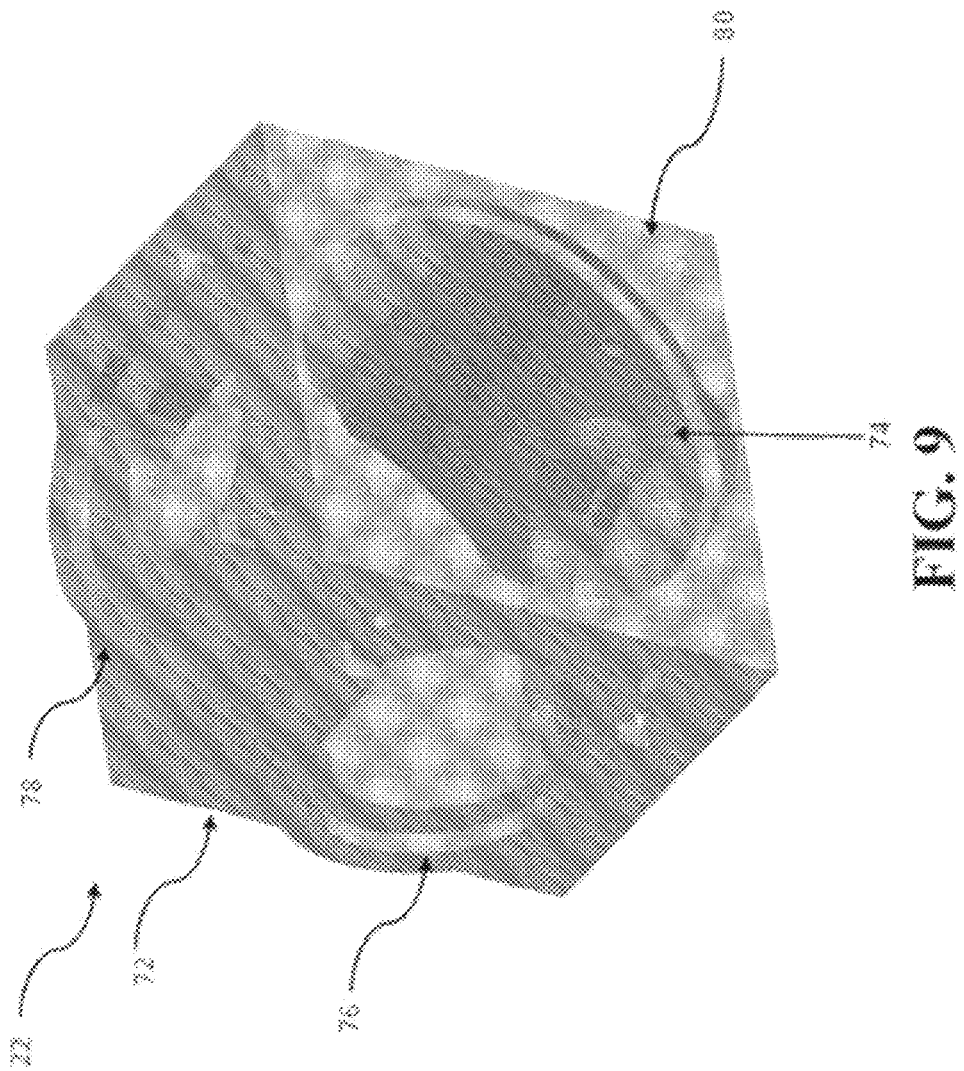
FIG. 9 is a perspective view of a filter housing of the microscope system of FIGS. 2A and 2B.

Referring now to FIG. 9, a filter housing 22 according to one aspect of the present disclosure is shown. Filter housing 22, which may be 3D printed as indicated above, includes a body 72 having a first side 74 configured to couple to end 30 of camera tube 18, a second side 76 configured to couple to end 44 of light source housing 34, a third side 78 configured to couple to end 60 of objective holder 54, and a fourth side 80 configured to receive a dichroic mirror holder as described below. In this configuration, excitation light from the LED enters filter housing 22 at a right angle to the image acquisition axis which extends longitudinally through objective holder 54. The dichroic mirror 23 (in FIGS. 2A and 2B) is held by the dichroic mirror holder (described below) at approximately a 45 degree angle relative to the entry angle of the excitation light to reflect the light through the objective holder 54 along the image acquisition axis. As indicated above, as the mirror is transparent to the light emitted by the tissue and acquired via image fiber optic 16, that light passes through the mirror and camera tube 18 to image acquisition device 12, which may display the captured image on display 252 of FIGS. 2A and 2B.

Figure 10:
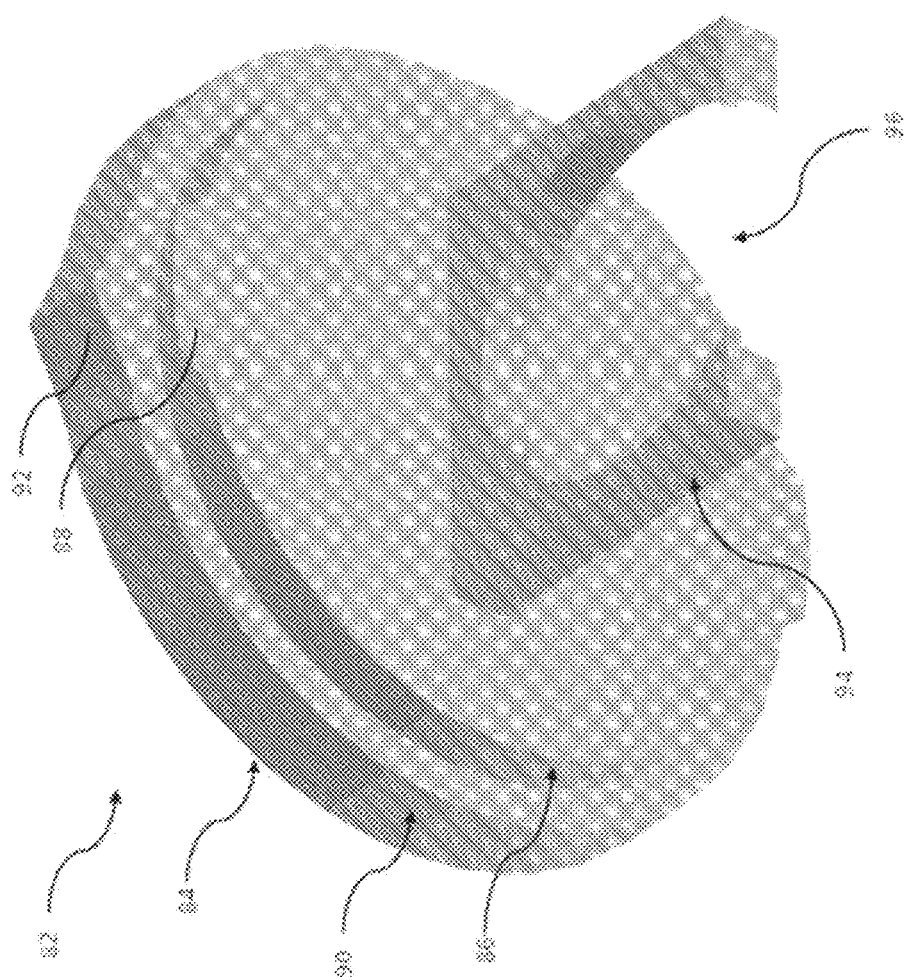
FIG. 10 is a perspective view of a dichroic mirror holder of the microscope system of FIGS. 2A and 2B.

FIG. 10 depicts one aspect of a dichroic mirror holder 82 of the present disclosure. Holder 82 includes a body 84 having an inner disc 86 with tabs 88, an outer disc 90 with tabs 92, and a mirror mount 94 that extends perpendicularly from inner disc 86. Mirror mount 94 includes an opening 96 for receiving the dichroic mirror. As should be apparent from the foregoing, inner disc 86 fits into the opening formed in fourth side 80 of filter housing 22 with tabs 88 in the annular slot formed around the opening and outer disc 90 and tabs 92 adjacent the outer surface of fourth side 90. In this manner, mirror mount 94 is supported within filter housing 22 and the angle of mirror mount 94 (and therefore the dichroic mirror) may be adjusted by rotating holder 82 within the opening of fourth side 80.

Figure 11:
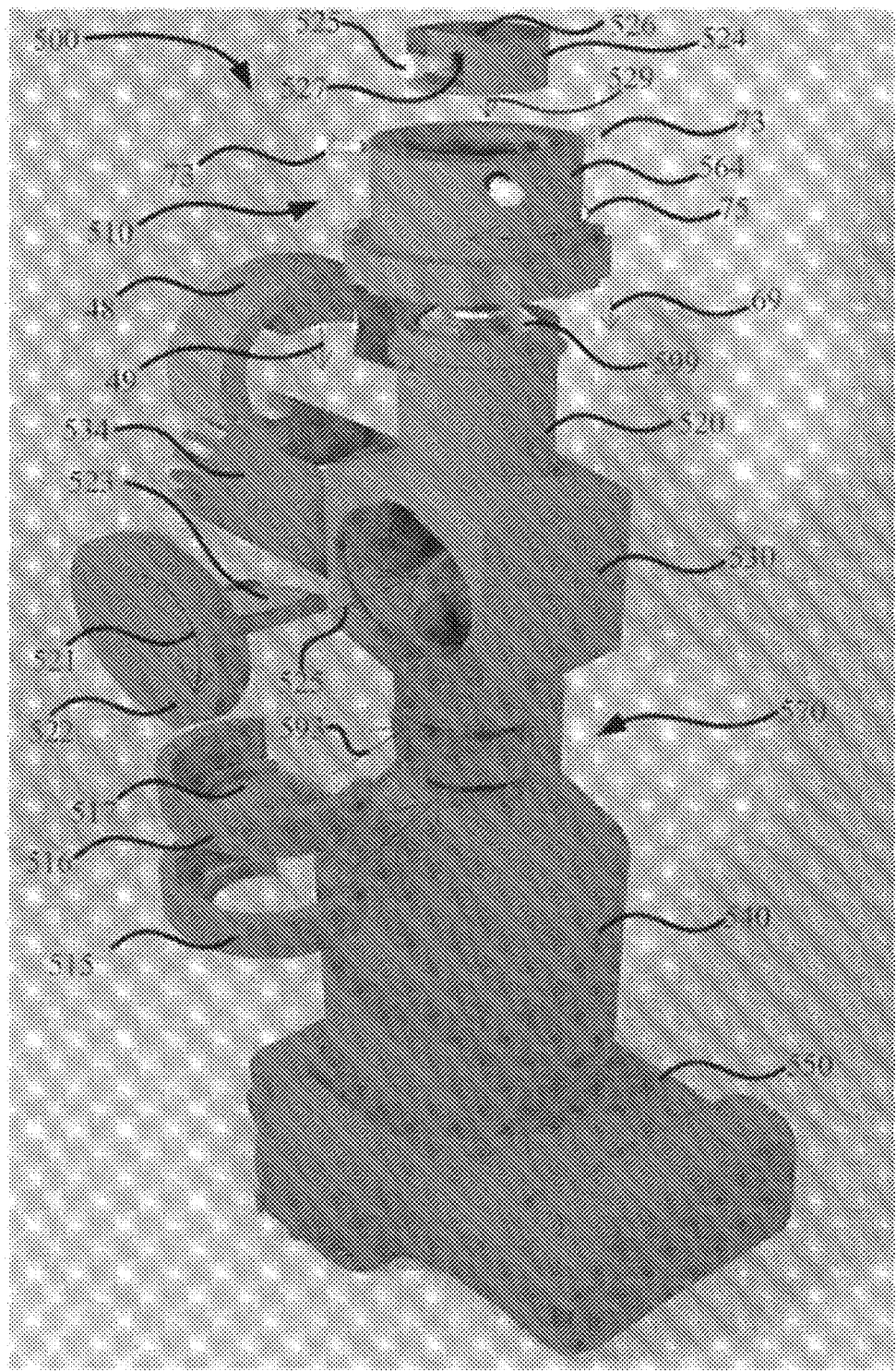
FIG. 11 is an expanded view of a microscope system according to various aspects.

FIG. 11 depicts microscope 500 according to various aspects. Microscope 500 may comprise an adapter 510. In various aspects, the adapter 510 may include a fiber-optic connecter 524 that may be mounted in an adjustment connector 564. Fiber-optic connector 524 may include a fiber-optic bore 526 that may be configured to accept a fiber-optic cable and a fiber-optic securing pin 525 that may pass through securing bore 527 may hold fiber-optic 16 (e.g., shown in FIGS. 13 and 14B) in place.

In various aspects, the adjustment connector 564 may be or include a lateral adjustment connector and/or a vertical adjustment connector. For example, with the exemplary aspect of FIG. 11, adjustment connector 564 may comprise lateral adjustment pins 73 which may help to secure fiber-optic connector 524 and may help to position and/or move the fiber-optic connector 524 laterally along the image acquisition axis (e.g., in direction 529). Thus, various aspects of adaptors include a lateral adjustment connector in mechanical communication with the fiber-optic connecter 526, wherein the lateral adjustment connecter is configured to adjust the fiber-optic connecter laterally.

Furthermore, the adapter may include or be a vertical adapter configured to move the fiber-optic connecter 526 along an image acquisition axis. With continued reference to FIG. 11, adapter 510 may include adjustment connector 564 (e.g., as described above). For example, the base of imaging fiber optic 16 may be adjusted toward and away from the objective lens by rotating fiber optic adapter 564 to permit focusing of excitation light into imaging fiber optic 16 and the light emitted from the base (e.g., proximal end) of imaging fiber optic 16 to the objective lens.

For example, adapter 510 may be configured to mechanically communicate with objective holder 520, which may hold objective 599. In various aspects, as adapter 510 rotates around the image acquisition axis (shown as direction 75), adapter 510 may move vertically along the image acquisition axis (e.g., in direction 69).

In various aspects, the image acquisition axis and an optical axis of an objective 599 in mechanical communication with the objective holder 520 may be aligned when the adapter is coupled to the objective holder 520. The objective is not particularly limited and may include any conventional or custom made objective (e.g., a 20× or 40× objective). Thus, various microscopes 500 may have an objective holder 520 that is configured to mechanically communicate with a 20× objective or 40× objective. In various embodiments, the objective holder 520 may form part of the microscope body 750.

Moreover, as described above, various aspects of the microscopes and systems described herein may have an adapter that is configured to transport an ablative energy along (e.g., parallel to the image axis) the image acquisition axis. The ablative energy is not particularly limited and may include optically transmissible energy from lasers, light emitting diodes, or combinations thereof.

Thus, various aspects of the systems and methods disclosed herein include simultaneous diagnosis and treatment of specimens with ablation. A skilled artisan—with the benefit of this disclosure—would recognize that the various known and hereinafter discovered ablation methods and systems may be adapted based on the treatment desired.

Figure 12:
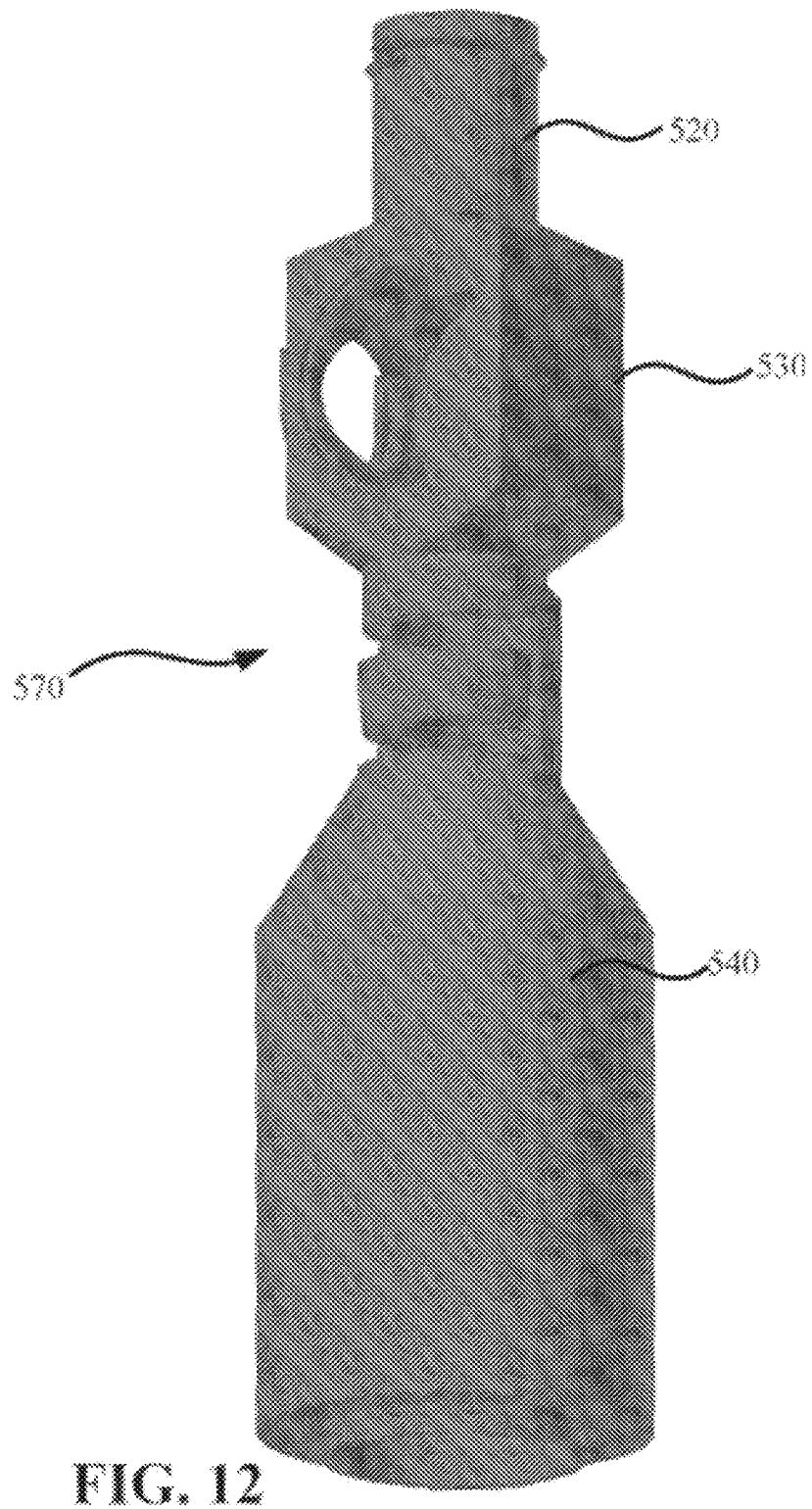
FIG. 12 depicts an integral microscope body according to various aspects.

Microscope 500, may also include microscope body 570, which may include objective holder 520, mirror holder 530, and body 540. In various aspects, the microscope body 570 may be one integral piece, such as exemplified in FIG. 12. In various aspects, filter holder may include dichroic mirror 523 held by filter source cap 522, which may be configured to mechanically communicate with mirror holder 530 (e.g., when turned in direction 521 to move laterally in direction 528).

Various systems and microscopes may also comprise a filter 517, filter holder 516 and tube lens holder 515, which may allow for the interchanging of various lenses (e.g. lens 218 shown in FIG. 2) and filters (e.g., via placement in direction 593) according to various aspects. The microscope 500 may also comprise an image acquisition device 550. The microscope 500 is not particularly limited and an ordinary skilled artisan may appreciate—with the benefit of this disclosure—that various aspects may include varying distances between various parts of the systems disclosed herein.

For example, the ratio X that may be between about 0.5 and about 1.5, between about 0.75 and about 1.25, between about 0.75 and 1.5, between about 0.5 and about 1.25, or about 1–according to various aspects—where the ratio X is defined as below:

$$X = \frac{\text{Distance from a proximal end of the fiber-optic and the tube lens}}{\text{Distance from the tube lens and the image acquisition device}}.$$

Figure 13:
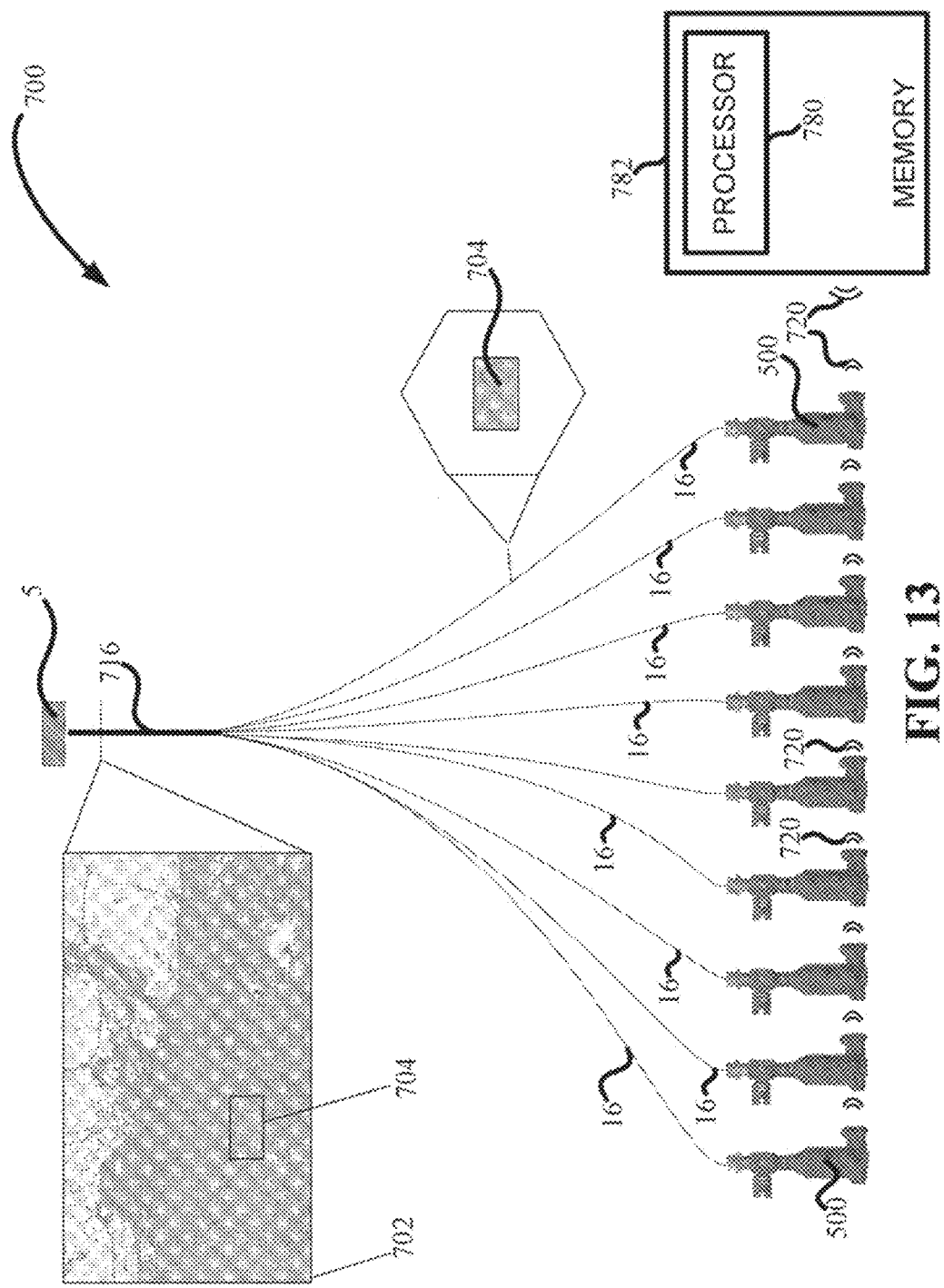
FIG. 13 depicts a system comprising a plurality of microscopes.

FIG. 13 depicts system 700 which may include a plurality of fluorescent microscopes 500, wherein a first fluorescent microscope comprises a first fiber-optic adapter connected to a first fiber-optic 16 and a second fluorescent microscope comprises a second fiber-optic adapter connected to a second fiber-optic 16, wherein the first fiber-optic and the second fiber-optic are in mechanical communication (e.g., to form fiber-optic bundle 716). Similar to the microscopes and adapters described above, system 700 may comprise one or more adapters where the adapter includes a fiber-optic connecter, a lateral adjustment connector in mechanical communication with the fiber-optic connecter. In various aspects, the lateral adjustment connecter may be configured to adjust the fiber-optic connecter laterally and a vertical adapter may be configured to move the fiber-optic connecter along an image acquisition axis, e.g. as described in detail herein.

As depicted in FIG. 13, system 700 may comprise at least one fluorescent microscope 500 that has an objective having an objective field of view 704. The objective field of views for each fiber-optic 16 that form part of fiber-optic bundle 716 may be combined to form a larger field of view 702 (e.g., a mosaic or composite of the field of view of each fiber-optic 16 that forms fiber-optic bundle 716).

Processor(s) 780 includes any suitable processing device or devices operative to execute the software/firmware stored at non-transitory memory 782. For example, processor 780 may include one or more programmable processors (e.g., central processing unit (CPU) devices), application-specific integrated circuits (ASICs), field-programmable gate arrays (FPGAs), digital signal processors (DSPs), hardwired logic, or combinations thereof.

In various aspects, at least one fluorescent microscope 500 of the plurality of fluorescent microscopes may have a ratio X that may be between about 0.5 and about 1.5, between about 0.75 and about 1.25, between about 0.75 and 1.5, between about 0.5 and about 1.25, or about 1, where the ratio X is defined as:

$$X = \frac{\text{Distance from a proximal end of the fiber-optic and the tube lens}}{\text{Distance from the tube lens and the image acquisition device}}.$$

Furthermore, the fiber optics 16 may be combined to form fiber-optic bundle 716. Thus, each fiber-optic 16 may be a bundle of small individual optical fibers and fiber-optic bundle 617 is a bundle of two or more fiber-optics 16. In various aspects, the alteration of the angle and/or the light through fiber-optics 16 onto specimen 5 may allow for system 500 to generate a three-dimensional image, such as a three-dimensional image. The plurality of fiber-optics may also be configured to alter a viewing angle, a field of view, or both.

Moreover, system 700 may also include at least one or more channels for ablative energy, such as through each microscope 500. In various aspects, the fiber optic 16 may be configured to channel ablative energy. As described above, the ablative energy is not particularly limited and may include radiofrequency (RF) energy, thermal cryoablative energy (cryoablation), lasers, or combinations thereof.

In various aspects, having a larger field of view 702 may allow for the simultaneous diagnosis and treatment of diseased tissue. For example, where ablative energy is capable of being channeled through each fiber-optic 16 of the fiber-optic bundle 716, treatment may occur with little to no damage to healthy tissue, thus minimizing recovery time, improving efficiency and accuracy of procedures, and improving verification of treatment success.

Figure 14A:
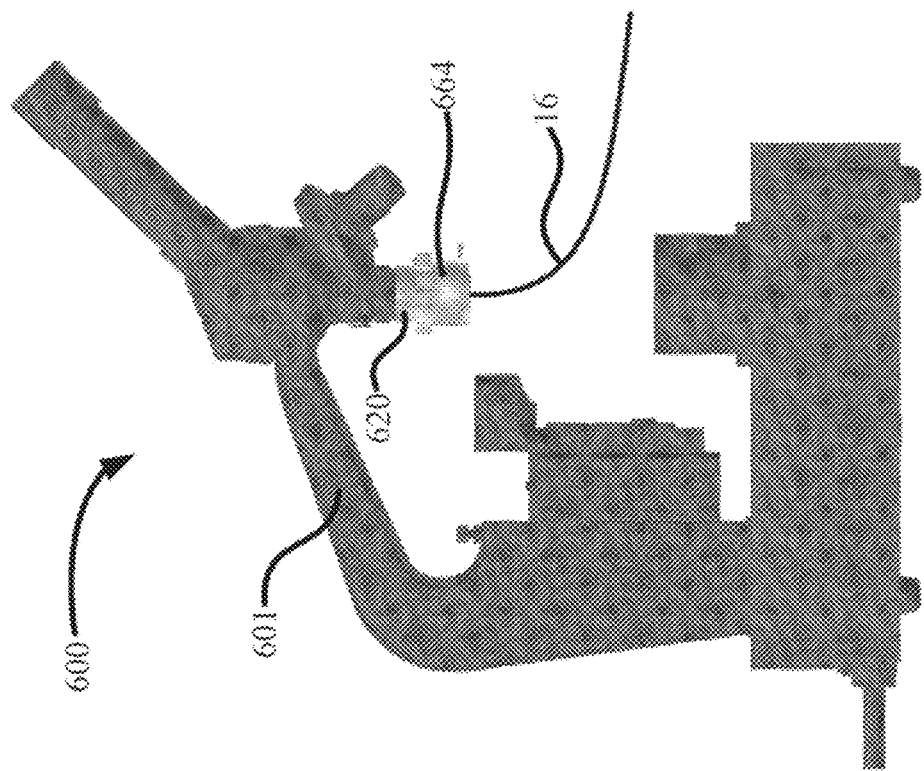
FIGS. 14A and 14B depict another aspect of a microscope system according to various aspects.
Figure 14B:
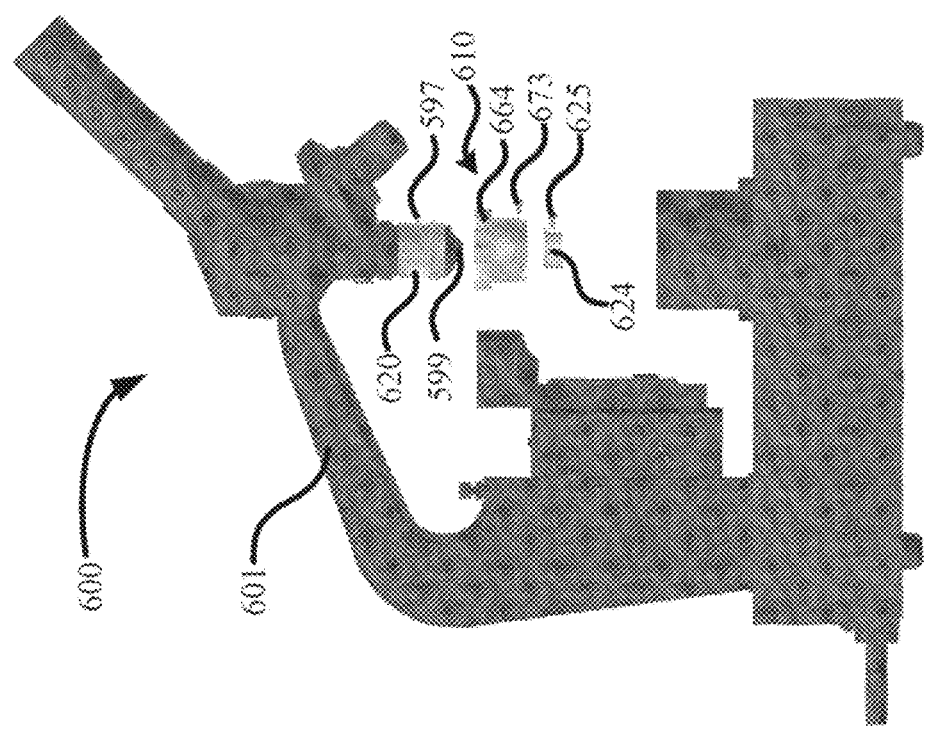

FIGS. 14A and 14B depict microscope system 600 according to various aspects. System 600 may comprise microscope 601 with the stage removed. FIG. 14A depicts the adaptor 610 in an expanded view, while FIG. 14B depicts the adapter 610 in place with fiber-optic 16 secured to the adapter 610. As shown in FIG. 14B, adapter 610 may comprise objective holder 620. Adapter 610 may also include fiber-optic connector 624, which may include a fiber-optic bore (shown in FIG. 15 as bore 526) that may be configured to accept a fiber-optic cable 16 and a fiber-optic securing pin 625. Also, adapter 664 may include lateral adjustment pins 673 to move fiber-optic connector 624 laterally with respect to the image acquisition axis.

Figure 15:
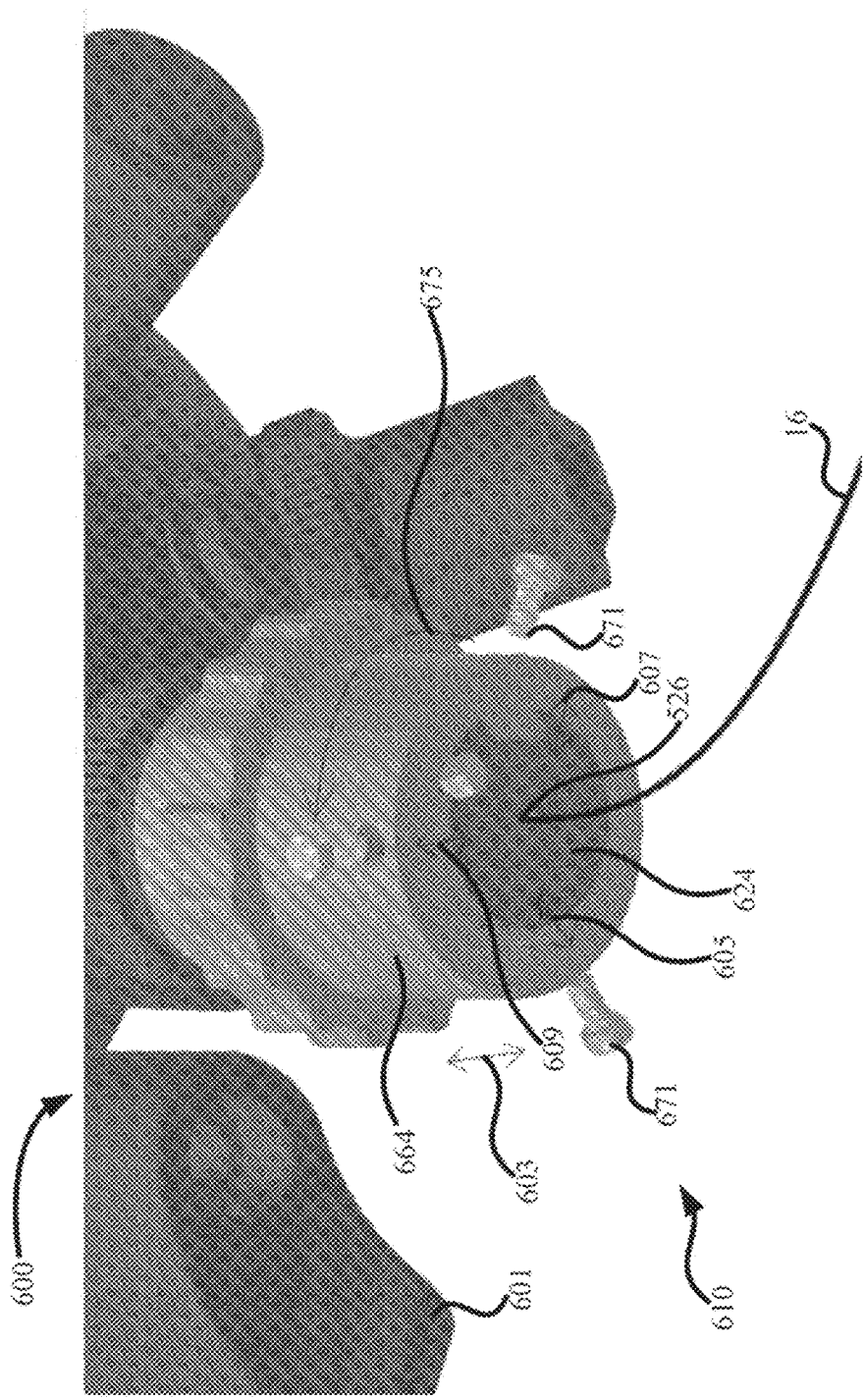
FIG. 15 is a perspective view of an adapter.

For example, FIG. 15 illustrates how the movement of pins 671 may cause fiber-optic connector 624 to move laterally in directions 605, 607, and 609. In some aspects, adapter 610 may be configured to move laterally along the image acquisition axis—along direction 603—when rotated around the image acquisition axis (shown as direction 675).

Figure 16:
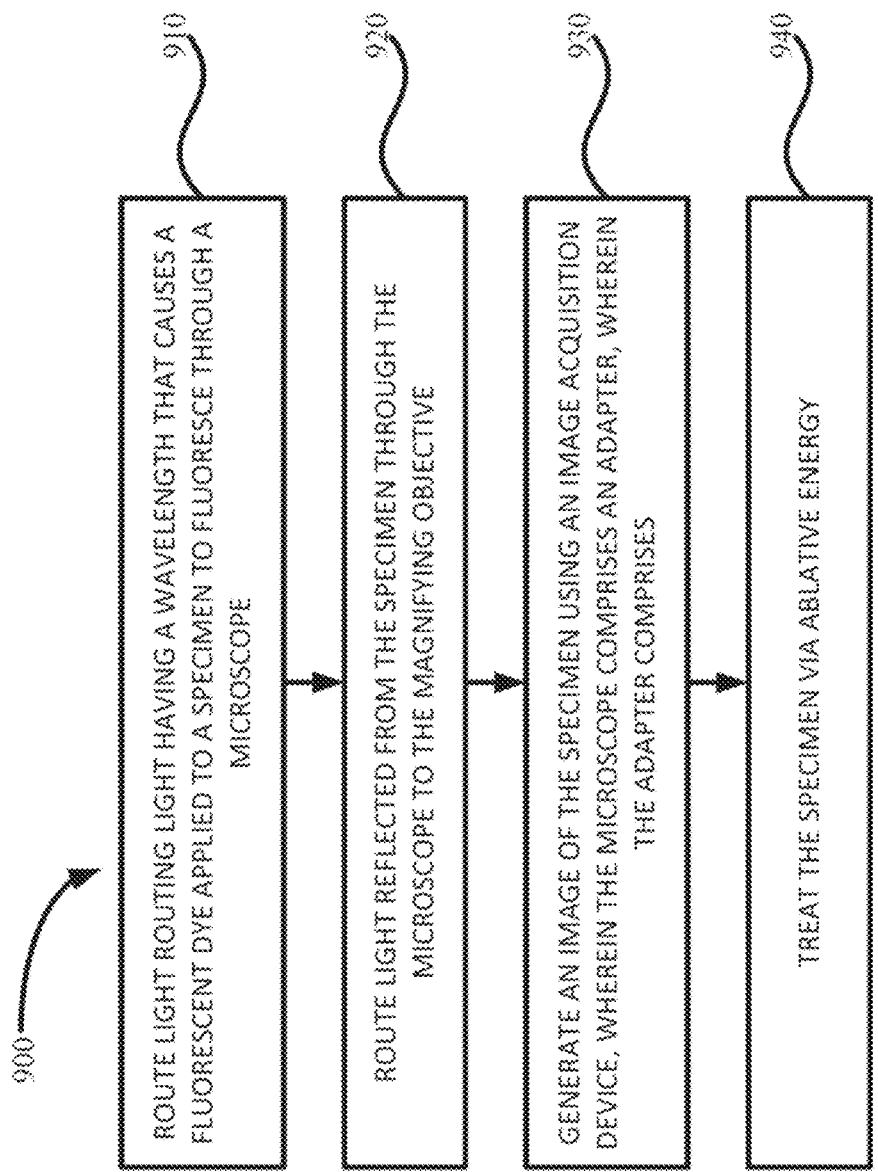
FIG. 16 depicts a method of evaluating and treating a specimen.

Also disclosed herein are various methods for evaluating a specimen, such as method 900 depicted in FIG. 16. Method 900 may include routing a first light having a wavelength that causes a fluorescent dye applied to a specimen to fluoresce through a microscope having an imaging fiber optic coupled to a magnifying objective and having a distal tip disposed adjacent the specimen (step 910). Then, a second light reflected from the specimen may be routed through the microscope to the magnifying objective (step 920) and then an image of the specimen using an image acquisition device may be generated (step 930). The method may also include treating the specimen via ablative energy (step 940).

The microscope is not particularly limited to any aspect described herein and may comprise an adapter. The adapter may include a fiber-optic connecter, a lateral adjustment connector in mechanical communication with the fiber-optic connecter, wherein the lateral adjustment connecter is configured to adjust the fiber-optic connecter laterally, and a vertical adapter configured to move the fiber-optic connecter along an image acquisition axis.

In the foregoing specification, specific aspects of the present disclosure have been described. However, one of ordinary skill in the art will appreciate that various modifications and changes can be made without departing from the scope of the disclosure as set forth in the claims below. Accordingly, the specification and figures are to be regarded in an illustrative rather than a restrictive sense, and all such modifications are intended to be included within the scope of disclosure. The benefits, advantages, solutions to problems, and any element(s) that may cause any benefit, advantage, or solution to occur or become more pronounced are not to be construed as critical, required, or essential features or elements of any or all the claims. The disclosure is defined solely by the appended claims including any amendments made during the pendency of this application and all equivalents of those claims as issued. Although the disclosure has been described in detail with reference to certain preferred aspects, variations and modifications exist within the spirit and scope as described and defined in the following claims.

What is claimed is:

1. An adapter for a microscope comprising:
   a fiber-optic connecter;
   a lateral adjustment connector in mechanical communication with the fiber-optic connecter, wherein the lateral adjustment connecter is configured to adjust the fiber-optic connecter laterally;
   a vertical adapter configured to move the fiber-optic connecter along an image acquisition axis; and
      wherein the microscope comprises a tube lens and an image acquisition device; and has a ratio X that is between 0.5 and 1.5, where $$X = \frac{\text{Distance from a proximal end of the fiber-optic and the tube lens}}{\text{Distance from the tube lens and the image acquisition device}}.$$

2. The adapter of claim 1, wherein the adapter is configured to mechanically communicate with an objective holder.

3. The adapter of claim 2, wherein the image acquisition axis and an optical axis of an objective in mechanical communication with the objective holder are aligned when the adapter is coupled to the objective holder.

4. The adapter of claim 2, wherein the objective holder is configured to mechanically communicate with a 20× objective.

5. The adapter of claim 1, wherein the adapter is configured to transport an ablative energy along the image acquisition axis.

6. The adapter of claim 5, wherein the ablative energy ablative is energy from a laser, light emitting diode, optically transmitted radiation or a combination thereof.

7. A system comprising:
a plurality of fluorescent microscopes, wherein a first fluorescent microscope comprises a first fiber-optic adapter connected to a first fiber-optic; and a second fluorescent microscope comprises a second fiber-optic adapter connected to a second fiber-optic, wherein the first fiber-optic and the second fiber-optic are in mechanical communication; and
wherein the at least one fluorescent microscope of the plurality of fluorescent microscopes comprises a tube lens and an image acquisition device; and
has a ratio X that is between 0.5 and 1.5, where $$X = \frac{\text{Distance from a proximal end of the fiber-optic and the tube lens}}{\text{Distance from the tube lens and the image acquisition device}}.$$

8. The system of claim 7, wherein the adapter includes a fiber-optic connecter;
a lateral adjustment connector in mechanical communication with the fiber-optic connecter, wherein the lateral adjustment connecter is configured to adjust the fiber-optic connecter laterally; and
a vertical adapter configured to move the fiber-optic connecter along an image acquisition axis.

9. The system of claim 8, wherein a field of view of the first fiber-optic and a field of view of the second fiber-optic form a larger field of view.

10. The system of claim 7, wherein a field of view of the first fiber-optic and a field of view of the second fiber-optic form a larger field of view.

11. The system of claim 10, further comprising a channel for ablative energy.

12. The system of claim 11, wherein the fiber optic is configured to channel the ablative energy.

13. The system of claim 12, wherein the ablative energy is a laser.

14. The system of claim 7, wherein the system is configured to generate a three-dimensional image.

15. The system of claim 7, wherein the system comprises a plurality of fiber-optics configured to alter a viewing angle, a field of view, or both.

16. A method for evaluating a specimen, comprising:
routing a first light having a wavelength that causes a fluorescent dye applied to a specimen to fluoresce through a microscope having an imaging fiber optic coupled to a magnifying objective and having a distal tip disposed adjacent the specimen;
wherein the at least one fluorescent microscope of the plurality of fluorescent microscopes comprises a tube lens and an image acquisition device; and
has a ratio X that is between 0.5 and 1.5, where $$X = \frac{\text{Distance from a proximal end of the fiber-optic and the tube lens}}{\text{Distance from the tube lens and the image acquisition device}};$$

routing a second light reflected from the specimen through the microscope to the magnifying objective; and
generating an image of the specimen using an image acquisition device, wherein the microscope comprises an adapter, wherein the adapter comprises:
a fiber-optic connecter,
a lateral adjustment connector in mechanical communication with the fiber-optic connecter, wherein the lateral adjustment connecter is configured to adjust the fiber-optic connecter laterally, and
a vertical adapter configured to move the fiber-optic connecter along an image acquisition axis.

17. The method of claim 16, wherein the specimen is treated via ablative energy.

* * * * *